United States Patent
Rødseth

(10) Patent No.: US 6,725,511 B1
(45) Date of Patent: Apr. 27, 2004

(54) JAW SUPPORTING DEVICE FOR USE ON A DECEASED PERSON

(76) Inventor: Kåre Roger Rødseth, N-6082 Gursken (NO)

( * ) Notice: Subject to any disclaimer, the term of this patent is extended or adjusted under 35 U.S.C. 154(b) by 0 days.

(21) Appl. No.: 09/869,227

(22) PCT Filed: Feb. 4, 2000

(86) PCT No.: PCT/NO00/00040
§ 371 (c)(1),
(2), (4) Date: Jun. 25, 2001

(87) PCT Pub. No.: WO00/45755
PCT Pub. Date: Aug. 10, 2000

(30) Foreign Application Priority Data

Feb. 5, 1999 (NO) .......................................... 19990539

(51) Int. Cl.[7] .......................... A01N 1/00; A61G 15/00
(52) U.S. Cl. ........................................ 27/25.1; 128/845
(58) Field of Search .............................. 27/25.1, 21.1; 128/845

(56) References Cited

U.S. PATENT DOCUMENTS

| | | | | |
|---|---|---|---|---|
| 506,886 A | * | 10/1893 | Sexton | |
| 1,051,896 A | * | 2/1913 | Kirkpatrick | |
| 1,397,499 A | * | 11/1921 | Brennan | |
| 2,000,344 A | * | 5/1935 | McClellan | |
| 2,088,207 A | * | 7/1937 | Kaiser | |
| 2,091,759 A | * | 8/1937 | Johnson | |
| 3,283,755 A | * | 11/1966 | Harden | |
| 4,538,597 A | * | 9/1985 | Lerman | |
| 4,712,540 A | * | 12/1987 | Tucker et al. | |
| 5,038,759 A | * | 8/1991 | Morgenstern | |

* cited by examiner

Primary Examiner—Weilun Lo
Assistant Examiner—Jacqueline F Stephens
(74) Attorney, Agent, or Firm—Rodman & Rodman

(57) ABSTRACT

The jaw supporting device for use on a deceased person is a one-piece, U-shaped jaw rest for resting against and gripping around the front of the neck of the deceased person. The U-shaped element has a curved portion at the bottom of the U-shape, with the curved portion having an upper side and a lower side. A jaw rest portion is formed at the upper side of the curved portion for engaging and supporting the jaw of the deceased person when the U-shaped element is positioned against the front of the neck of the deceased person. A chest or collar engaging portion can be formed at the lower side of the curved portion for engaging against the chest or collar bone when the U-shaped element is positioned against the front of the neck of the deceased person.

8 Claims, 5 Drawing Sheets

JAW SUPPORTING DEVICE FOR USE ON A DECEASED PERSON

BACKGROUND OF THE INVENTION

The present invention relates to a jaw rest for supporting the jaw of a deceased person.

When a person dies the first phenomenon to occur is a complete relaxation of the body.

Where the jaw is concerned, this manifests itself in that it "falls down" towards the chin, resulting in the deceased person lying with a partly open mouth.

Before rigor mortis, literally "stiffness of death", sets in, normally after two to five hours, the jaw must therefore be pressed upwards manually, not least for aesthetic reasons, so that the mouth remains closed.

Normally, the solution to this problem is that during the preliminary preparation of the deceased use is made of a bandage that is usually a part of the kit which is used for attending to the bodies of the newly dead. This bandage is placed under the chin of the deceased person, laid over the cheek on either side and tied together or fastened on top of the head.

Many view this as a difficult process, and usually two persons are required to carry out this task so as to obtain a satisfactory result, i.e., one person presses the deceased person's jaw upwards and another places the bandage under the chin of the deceased and fastens it on the top of the head with a knot, safety pins, or with a form of self-adhesive/self-locking bandage.

Thus, this method of bandaging up the jaw of a deceased person has certain weaknesses, as can be heard from those with practical experience:

1. The process is difficult and the bandage is apt to be become loose and fall off.
2. There must often be two persons in order to obtain a satisfactory result.
3. In addition to being difficult for the carers, this process is also aesthetically rather unattractive as the deceased person is scarcely recognisable with the bandage on. The cheeks lie in folds, the hair is barely visible, and together these together mean that the bereaved family, who usually would like to see the deceased person immediately after death, do not "recognise" their departed family member. Thus, this is a far from pleasing and aesthetic way of presenting deceased persons.
4. Lastly, the carers or undertakers must often attend to the same dead person several times. This means to say that the first preparation of the body is done immediately after death, and it is at this point that the jaw is bound up in the described manner. Later it is often necessary to take the bandage off to do the hair and so forth when the bereaved family are to see the deceased person.

OBJECTS OF THE INVENTION

It is an object of the present invention to provide a device which will solve the aforementioned problems and replace the method of bandaging up the jaw used today.

It is an object of the invention to enable one person to put the jaw in place in the closed position simply and easily and in such manner that it remains there until rigor mortis has set in.

The jaw rest referred to in the introduction is characterised by the features disclosed in the patent claims.

A jaw rest of this kind according to the invention may have various forms as will be described in more detail below.

DESCRIPTION OF THE DRAWINGS

The invention will be described in more detail with reference to the accompanying drawings, wherein:

FIG. 1 shows a jaw rest 2 according to the invention, placed against and partly around the neck 3 and under the jaw 2.

FIG. 1 shows a jaw rest 2 according to the invention, placed against and partly around the neck 3 and under the jaw 1.

DETAILED DESCRIPTION

Figure 2A:
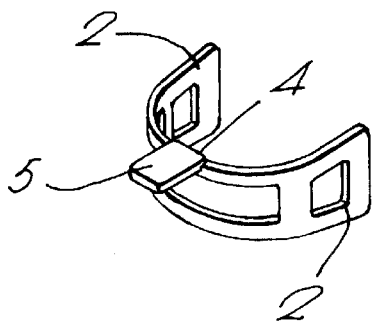
FIG. 2a is perspective view of the jaw rest of FIG. 1.
Figure 2B:
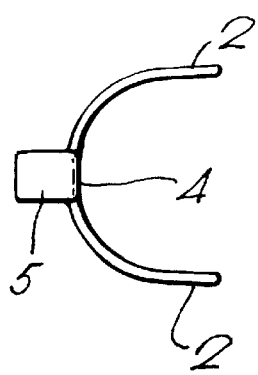
FIG. 2b is a top plan view thereof.
Figure 2C:
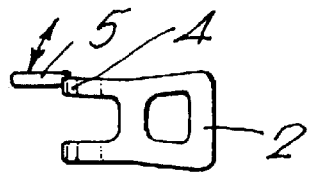
FIG. 2c is a side elevation thereof.

As can be seen from FIGS. 2a–2c, the illustrated embodiment is in the form of a U-shaped element which at an upper convex edge of the upper part 4 is equipped with an optionally projecting, preferably elastic support flange 5. Optionally, the flange is only bendable into the desired position.

The upper part 4 and the flange 5 may be in any shape provided they give sufficient support under the chin.

Figure 1:
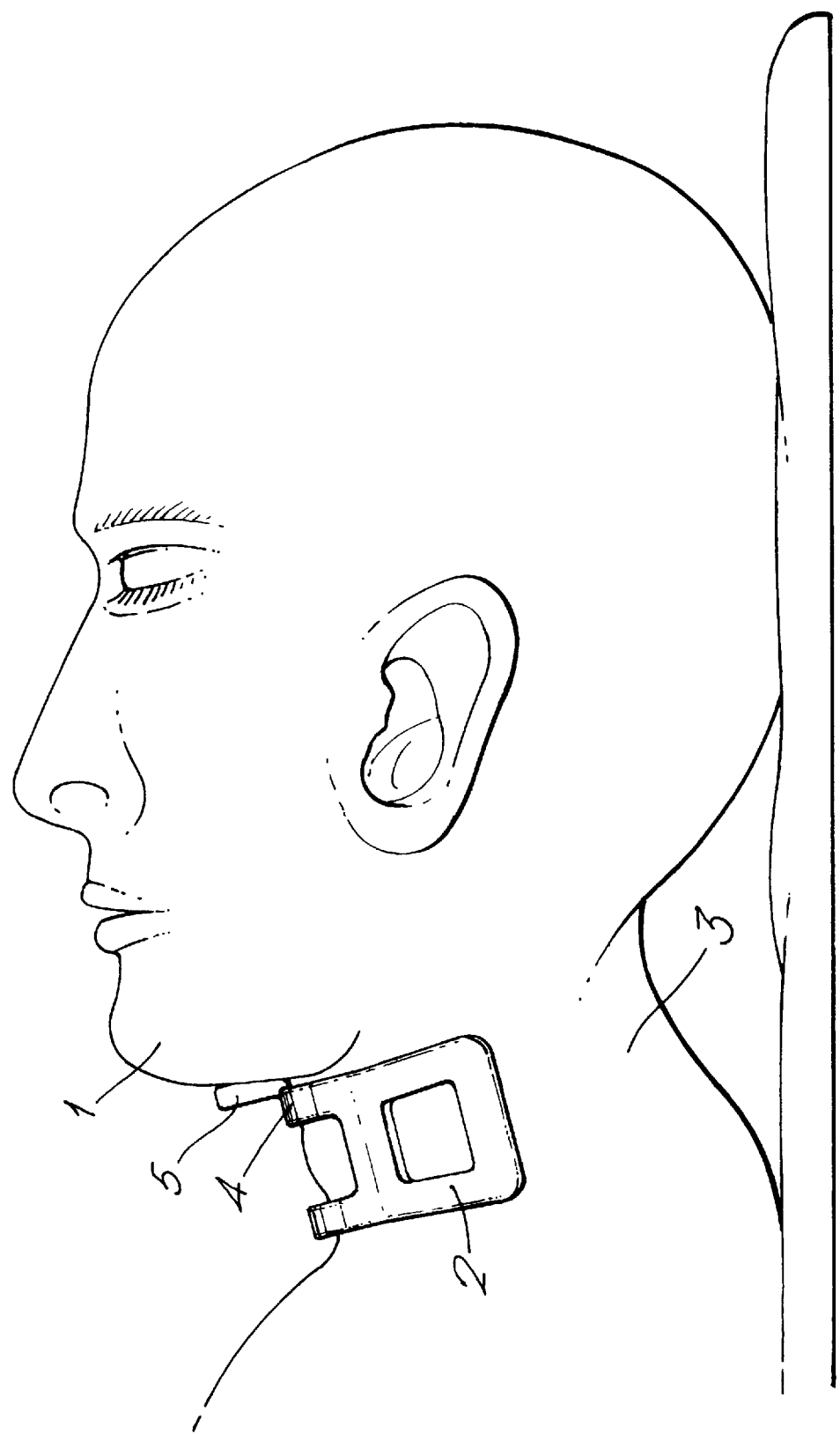
FIG. 1 shows jaw rest according to the invention, put in place.

In the embodiment shown in FIGS. 1 and 2, there is no enlarged portion designed to rest against the chest or collarbone.

The jaw rest in the embodiment shown in FIGS. 1 and 2 should have a certain elasticity to be able to grip firmly around the deceased person's neck and remain securely in place after it has been put in position. However, without going beyond the scope of the invention, it is conceivable that jaw rests according to the invention are equipped with tapes around the neck which can in a simple manner hold them in place.

The use of two-sided tape for fastening to the neck is also conceivable.

In one possible embodiment, the flange 5 may be shaped in the form of a disc, but nonetheless so that it comes to rest under the chin by turning or bending, and optionally because of its springiness.

A non-illustrated embodiment where a support bar is arranged between the outside of the element 2 and the underside of the flange 5 is also conceivable.

Figure 3A:
FIG. 3a is a perspective view of another embodiment of the invention.
Figure 3B:
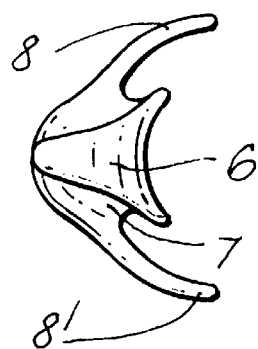
FIG. 3b is a top plan view thereof.
Figure 3C:
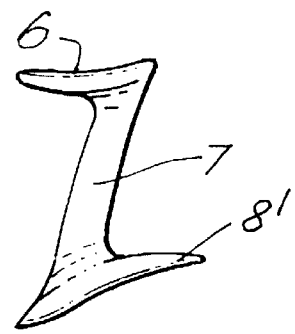
FIG. 3c is a side elevation thereof.

A possible embodiment of this kind is in principle shown in FIGS. 3a–3c where the upper part 6 is shaped in the form a disc on the element 7 in the form of a column, and where the encircling of the element 7 around the neck to a certain extent is provided by arms 8, 8', and wherein the part of the element 7 facing the neck 3 and the arms 8, 8' may, for example, be equipped with two-sided tape for better securement.

Figure 4A:
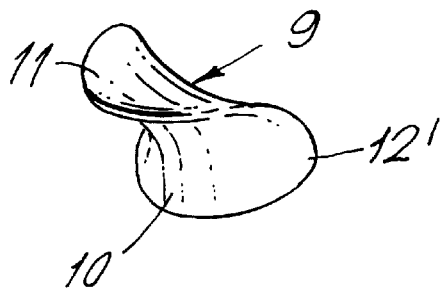
FIG. 4a is a perspective view of a further embodiment of the invention.
Figure 4B:
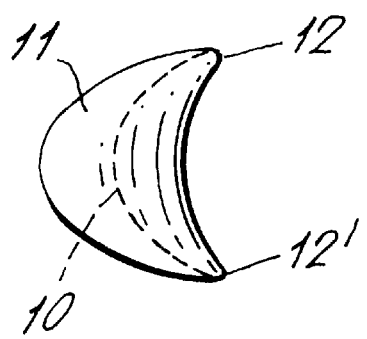
FIG. 4b is a top plan view thereof.
Figure 4C:
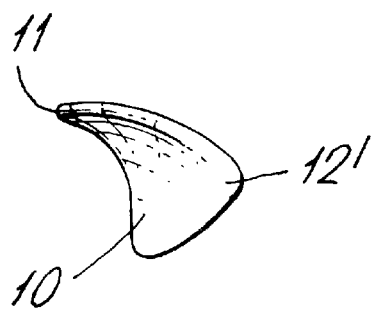
FIG. 4c is a side elevation thereof.

FIGS. 4a–4c shows another, simplified form where the body of an element 9 as shown in FIGS. 3a–3c is further shortened and at the same time made broader so that a lower part 10 designed to rest against the deceased person's chest and the upper part 11 designed to bear against and support the jaw 1 extend across the entire width of the element 9 and wherein the arms 12, 12' are formed by a form of "folding".

Figure 5A:
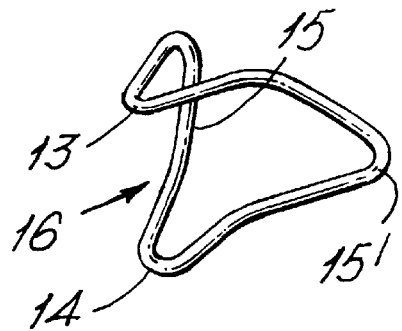
FIG. 5a is perspective view of still another embodiment of the invention.
Figure 5B:
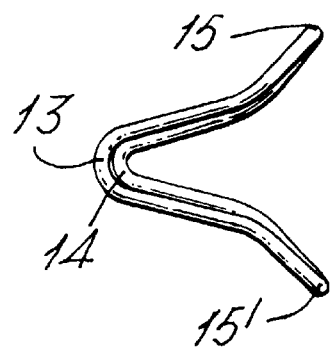
FIG. 5b is a top plan view thereof.
Figure 5C:
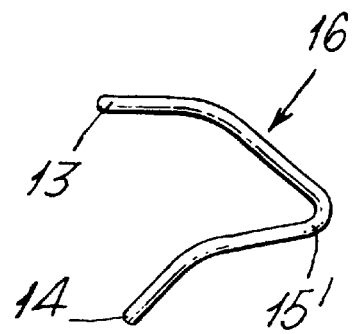
FIG. 5c is a side elevation thereof.

FIGS. 5a–5c show in principle a variant of the jaw rest which is shown in FIG. 4 and wherein only the "periphery" of the rest in FIG. 4 is maintained in the form of an elastic material with respectively an upper part 13 and a lower part 14 and arms 15, 15' in the form of U-shaped side pieces, all integral in the form of an elastic element 16.

Whilst the rests in FIGS. 3 and 4 may advantageously be provided with better securement by using two-sided tape, it may be beneficial, depending on the length of the arms 6 on the rest as shown in FIG. 5 to have an extra tape around the neck of the deceased person.

FIGS. 2, 3, 4, 5, 6 and 7 show six possible embodiments, but it is of course possible to conceive of more possibilities for variation without departing from the spirit and scope of the invention as it has been outlined above and defined in the claims.

Figure 6:
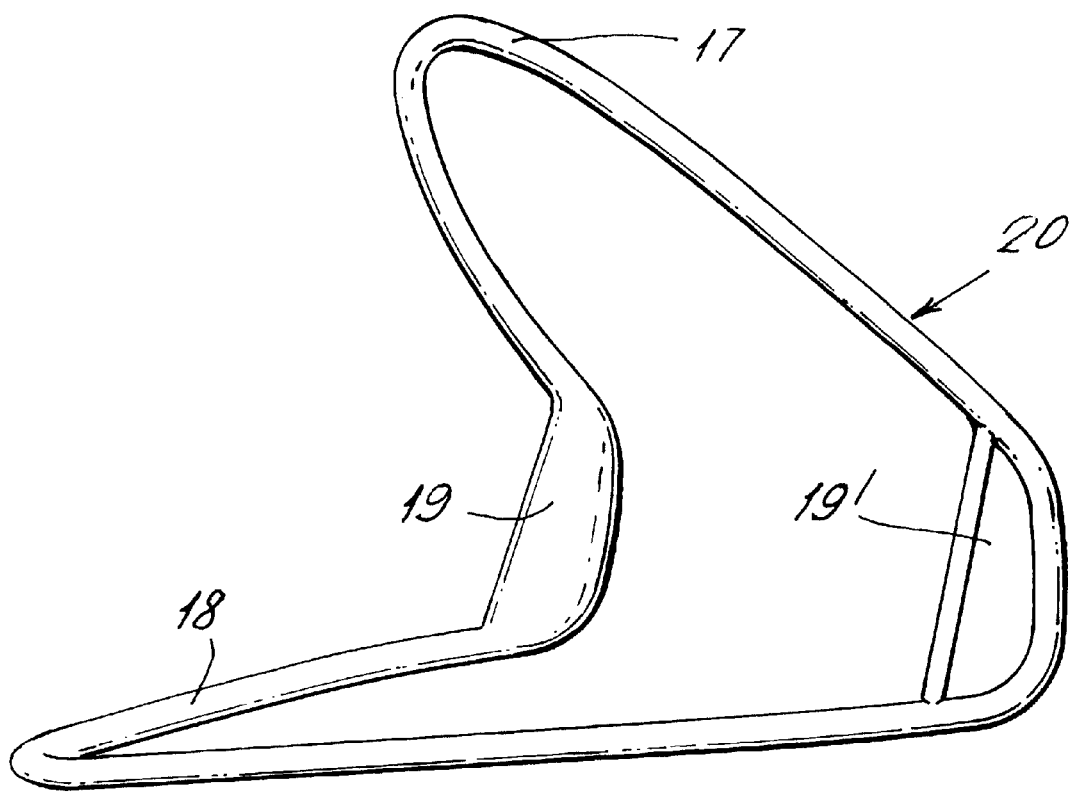
FIGS. 6 and 7 show typical commercial embodiment variants of the jaw rest.

In FIG. 6 the jaw rest 20 has a curved jaw rest part 17 and a collarbone or chest rest part 18, and a portion 19, 19' between these parts which may either be stiff or be slightly elastic.

Figure 7:
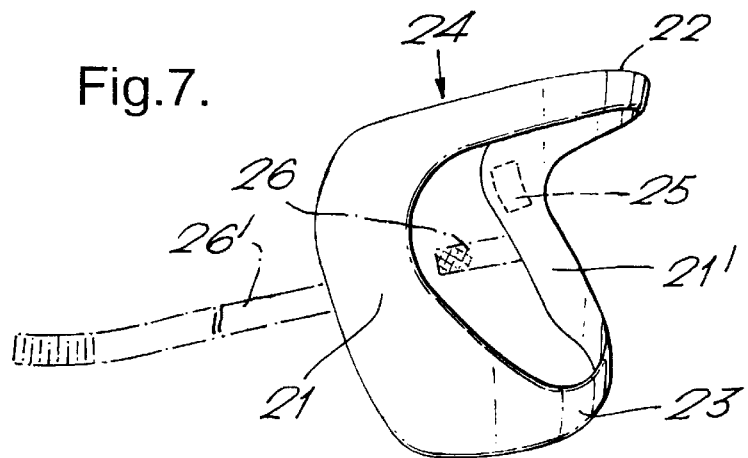
Figure 8:
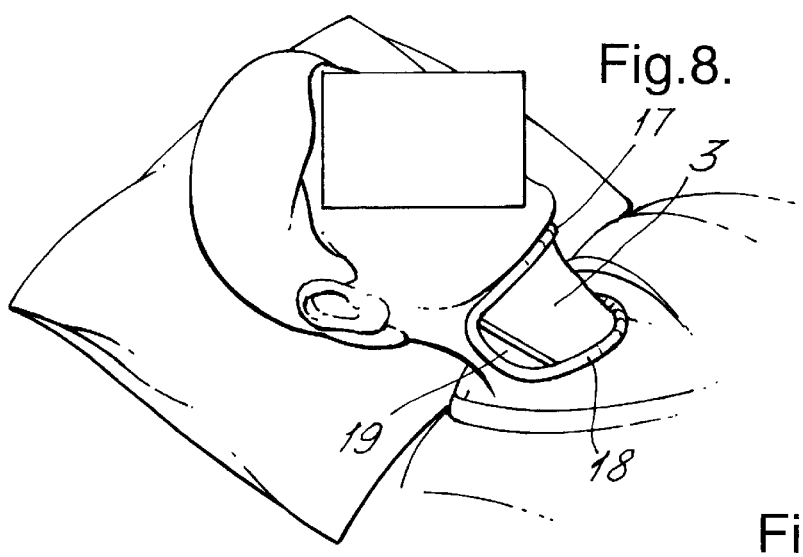
FIGS. 8 and 9 show a typical placement of the jaw rest on a deceased person.
Figure 9:
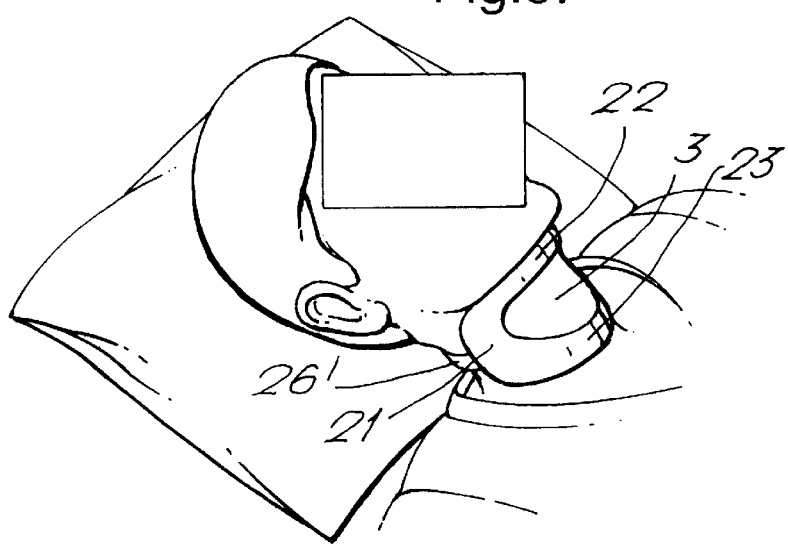

FIG. 7 shows a variant of the rest, for example, made of plastic, cardboard or another suitable material which by means of its wide side portions 21, 21' provide the necessary stiffness in the jaw rest between a jaw rest part 22 and a collarbone/chest rest part 23. It is also conceivable that this jaw rest 24 could be supplied as a flat piece which can be bent so as to allow the portions 21, 21' to rest against the dead person's neck 3, whereupon the rest 24 can be fastened to the deceased's neck 3 using two-sided adhesive tape, plaster or the like.

The portions 21, 21' of the jaw rest 24 may optionally be equipped with two-sided adhesive tape, for fastening to the neck 25 of the deceased person.

As an alternative, the fastening of the rest 24 can be done using means which permit fastening around the neck, for example a strap 26, 26' equipped with Velcro® tape.

A jaw support according to the invention has the following advantages:

1) it is hardly visible;
2) the face and hair of the deceased person are not covered;
3) the hair can be done so that the deceased person can be recognised more easily;
4) the shape of the face is kept intact, i.e., folds are not formed in the cheeks as is the case with the bandaging used to date;
5) it is sufficient to prepare the corpse once; it is not necessary to do the job several times; and
6) the process is simpler for the carer and can be done by one person.

The rest according to the invention can be made of any suitable material, provided that the purely mechanical requirements are met. However, it is of course an advantage if a biodegradable material can be used.

The rest according to the invention will represent a considerable simplification and easing of their work for those responsible for the preparation of the bodies of the newly dead.

Furthermore, the rest according to the invention will make it easier and less distressing to see the deceased person as the inventive rest can be made of a transparent or flesh-coloured material and in addition it will also be largely covered by the burial clothes or shroud.

The weaknesses mentioned at the beginning are remedied in a simple and aesthetic manner whilst a not entirely easy but nevertheless necessary job is made simpler.

What is claimed is:

1. A jaw rest for supporting the jaw of a deceased person comprising a preformed one-piece U-shaped element for resting against and gripping around the front portion of a neck of a deceased person, without being secured to or engaged with any other neck supporting member, said one-piece U-shaped element having a curved portion at the bottom of the U-shape, said curved portion being formed to make contact with the front portion of the neck, said curved portion having an upper side and a lower side and a jaw rest portion formed at the upper side of the curved portion for engaging and supporting the jaw of the deceased person when the U-shaped element is positioned against and in contact with the front portion of the neck of the deceased person.

2. The jaw rest as claimed in claim 1 wherein a chest or collarbone engaging portion is formed at the lower side of the curved portion for engaging against the chest or collar bone of the deceased person when the U-shaped element is positioned against the front portion of the neck of the deceased person.

3. The jaw rest as claimed in claim 1 wherein the jaw rest portion is in the form of a flange with resilient spring-like characteristics.

4. The jaw rest as claimed in claim 1, wherein the jaw rest is formed of a naturally degradable material.

5. The jaw rest as claimed in claim 1 including a two-sided adhesive tape secured to at least one portion of the surface of the U-shaped element that rests against the neck of the deceased person.

6. The jaw rest as claimed in claim 1 wherein said U-shaped element has spaced leg portions and a securement strap is secured to each of said leg portions for fastening around the neck of a deceased person.

7. The jaw rest as claimed in claim 6 wherein said securement straps include engageable hook and loop fasteners.

8. The jaw rest as claimed in claim 1 wherein the jaw rest portion is formed integrally with the U-shaped element.

* * * * *

UNITED STATES PATENT AND TRADEMARK OFFICE
CERTIFICATE OF CORRECTION

| | |
|---|---|
| PATENT NO. | : 6,725,511 B1 |
| DATED | : June 8, 2004 |
| INVENTOR(S) | : Kåre Roger Rødseth |

It is certified that error appears in the above-identified patent and that said Letters Patent is hereby corrected as shown below:

<u>Column 2,</u>
Line 31, delete "Fig. 1 shows a jaw rest 2 according to the invention placed against and partly around the neck 3 and under the jaw 2." insert therefor -- Fig. 1 shows a jaw rest 2 according to the invention, placed against and partly around the neck 3 and under the jaw 1. --.
Line 38, the title -- Detailed Description -- should appear after line 35.

Signed and Sealed this

Third Day of August, 2004

JON W. DUDAS
*Acting Director of the United States Patent and Trademark Office*